United States Patent
Aspnes et al.

(10) Patent No.: US 6,304,326 B1
(45) Date of Patent: *Oct. 16, 2001

(54) THIN FILM OPTICAL MEASUREMENT SYSTEM AND METHOD WITH CALIBRATING ELLIPSOMETER

(75) Inventors: David E. Aspnes, Apex, NC (US); Jon Opsal, Livermore; Jeffrey T. Fanton, Los Altos, both of CA (US)

(73) Assignee: Therma-wave, Inc., Fremont, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/247,121

(22) Filed: Feb. 8, 1999

Related U.S. Application Data

(63) Continuation of application No. 09/098,880, filed on Jun. 17, 1998, now Pat. No. 5,900,939, which is a continuation of application No. 08/890,697, filed on Jul. 11, 1997, now Pat. No. 5,798,837.

(51) Int. Cl.[7] ........................................... G01J 4/00
(52) U.S. Cl. ..................... 356/369; 356/381; 356/243.1
(58) Field of Search .................................. 356/364, 365, 356/366, 367, 368, 369, 381, 382, 243.1; 250/225

(56) References Cited

U.S. PATENT DOCUMENTS 3,824,017  7/1974  Galyon .............................. 356/108

(List continued on next page.)

FOREIGN PATENT DOCUMENTS 93 00 956 U    5/1993  (DE).

(List continued on next page.)

OTHER PUBLICATIONS

R.P. Netterfield et al., "Characterization of growing thin films by in situ ellipsometry, spectral reflectance and transmittance measurements, and ion–scattering spectroscopy," Rev. Sci. Instrum., vol. 56, No. 11, Nov. 1985, pp. 1995–2003.

(List continued on next page.)

Primary Examiner—Hoa Q. Pham
(74) Attorney, Agent, or Firm—Limbach & Limbach L.L.P.

(57) ABSTRACT

An optical measurement system for evaluating a reference sample that has at least a partially known composition. The optical measurement system includes a reference ellipsometer and at least one non-contact optical measurement device. The reference ellipsometer includes a light generator, an analyzer and a detector. The light generator generates a beam of quasi-monochromatic light having a known wavelength and a known polarization for interacting with the reference sample. The beam is directed at a non-normal angle of incidence relative to the reference sample to interact with the reference sample. The analyzer creates interference between the S and P polarized components in the light beam after the light beam has interacted with reference sample. The detector measures the intensity of the light beam after it has passed through the analyzer. A processor determines the polarization state of the light beam entering the analyzer from the intensity measured by the detector, and determines an optical property of the reference sample based upon the determined polarization state, the known wavelength of light from the light generator and the composition of the reference sample. The processor also operates the optical measurement device to measure an optical parameter of the reference sample. The processor calibrates the optical measurement device by comparing the measured optical parameter from the optical measurement device to the determined optical property from the reference ellipsometer.

28 Claims, 3 Drawing Sheets

U.S. PATENT DOCUMENTS

| | | | |
|---|---|---|---|
| 3,926,524 | 12/1975 | Marguiles et al. | 356/114 |
| 3,985,447 | 10/1976 | Aspnes | 356/118 |
| 4,053,232 | 10/1977 | Dill et al. | 250/225 |
| 4,155,009 | 5/1979 | Lieber et al. | 250/308 |
| 4,298,283 | 11/1981 | Makosch et al. | 356/351 |
| 4,309,103 | 1/1982 | Bodlaj | 356/1 |
| 4,332,476 | 6/1982 | Stenberg et al. | 356/369 |
| 4,492,456 | 1/1985 | Aspnes | 356/334 |
| 4,523,848 | 6/1985 | Gorman et al. | 356/368 |
| 4,606,641 | 8/1986 | Yamada et al. | 356/369 |
| 4,647,207 | 3/1987 | Björk et al. | 356/369 |
| 4,672,196 | 6/1987 | Canino | 250/225 |
| 4,681,444 | 7/1987 | Ferber et al. | 356/318 |
| 4,796,995 | 1/1989 | Salzman et al. | 356/368 |
| 4,872,758 | 10/1989 | Miyazaki et al. | 356/381 |
| 4,899,055 | 2/1990 | Adams | 250/372 |
| 4,905,170 | 2/1990 | Forouhi et al. | 364/556 |
| 4,929,078 | 5/1990 | Harmon | 356/320 |
| 4,931,132 | 6/1990 | Aspnes et al. | 156/601 |
| 4,969,740 | 11/1990 | Sonobe | 356/326 |
| 4,999,014 | 3/1991 | Gold et al. | 356/382 |
| 5,018,863 | 5/1991 | Vareille et al. | 356/369 |
| 5,042,951 | 8/1991 | Gold et al. | 356/369 |
| 5,091,320 | 2/1992 | Aspnes et al. | 437/8 |
| 5,101,111 | 3/1992 | Kondo | 250/560 |
| 5,120,966 | 6/1992 | Kondo | 250/372 |
| 5,131,752 | 7/1992 | Yu et al. | 356/369 |
| 5,181,080 | 1/1993 | Fanton et al. | 356/381 |
| 5,277,747 | 1/1994 | Aspnes | 156/626 |
| 5,296,913 | 3/1994 | Heffner | 356/364 |
| 5,298,973 | 3/1994 | Fukazawa et al. | 356/368 |
| 5,317,150 | 5/1994 | Norris et al. | 250/252.1 |
| 5,321,970 | 6/1994 | Davies et al. | 73/1 R |
| 5,329,357 | 7/1994 | Bernoux et al. | 356/369 |
| 5,337,150 | 8/1994 | Mumola | 356/382 |
| 5,365,334 | 11/1994 | Bottka | 356/326 |
| 5,371,586 | 12/1994 | Chau | 356/301 |
| 5,373,359 | 12/1994 | Woollam et al. | 356/328 |
| 5,408,322 | 4/1995 | Hsu et al. | 356/369 |
| 5,412,473 | 5/1995 | Rosencwaig et al. | 356/351 |
| 5,416,588 | 5/1995 | Ducharme et al. | 356/369 |
| 5,416,594 | 5/1995 | Gross et al. | 356/237 |
| 5,420,680 | 5/1995 | Isobe et al. | 356/128 |
| 5,444,528 | 8/1995 | Puschell | 356/73 |
| 5,452,091 | 9/1995 | Johnson | 356/445 |
| 5,485,082 | 1/1996 | Wisspeintner et al. | 324/202 |
| 5,485,271 | 1/1996 | Drevillon et al. | 356/345 |
| 5,489,980 | 2/1996 | Anthony | 356/308 |
| 5,521,705 | 5/1996 | Oldenbourg et al. | 356/368 |
| 5,521,706 | 5/1996 | Green et al. | 356/369 |
| 5,526,117 | 6/1996 | Wielsch et al. | 356/369 |
| 5,528,649 | 6/1996 | Heidsieck | 378/56 |
| 5,568,252 | 10/1996 | Kusuda et al. | 356/72 |
| 5,581,350 | 12/1996 | Chen et al. | 356/369 |
| 5,581,354 | 12/1996 | Hassbjer | 356/381 |
| 5,582,646 | 12/1996 | Woollam et al. | 118/708 |
| 5,596,406 | 1/1997 | Rosencwaig et al. | 356/327 |
| 5,596,411 | 1/1997 | Fanton et al. | 356/369 |
| 5,608,526 | 3/1997 | Piwonka-Corle et al. | 356/369 |
| 5,610,392 | 3/1997 | Nagayama et al. | 250/226 |
| 5,612,782 | 3/1997 | Keränen et al. | 356/243 |
| 5,615,009 | 3/1997 | Sakura et al. | 356/326 |
| 5,625,455 | 4/1997 | Nash et al. | 356/369 |
| 5,686,993 | 11/1997 | Kokubo et al. | 356/381 |
| 5,706,212 | 1/1998 | Thompson et al. | 356/368 |
| 5,739,909 | 4/1998 | Blayo et al. | 356/369 |
| 5,754,294 | 5/1998 | Jones et al. | 356/355 |
| 5,764,365 | 6/1998 | Finarov | 356/381 |
| 5,771,094 | 6/1998 | Carter et al. | 356/326 |
| 5,777,733 | 7/1998 | Radziuk | 356/328 |
| 5,835,221 | 11/1998 | Lee et al. | 356/369 |
| 5,900,939 | * 5/1999 | Aspnes et al. | 356/369 |
| 5,933,792 | 8/1999 | Andersen et al. | 702/32 |
| 5,956,145 | 9/1999 | Green et al. | 356/364 |

FOREIGN PATENT DOCUMENTS

| | | |
|---|---|---|
| 0 396 409 | 11/1990 | (EP) . |
| 0 503 874 A2 | 9/1992 | (EP) . |
| 0 652 415 | 5/1995 | (EP) . |
| 61-182507 | 8/1986 | (JP) . |
| 1023126 | 1/1989 | (JP) . |
| 5-71923 | 3/1993 | (JP) . |
| 5-93611 | 4/1993 | (JP) . |
| 5-133811 | 5/1993 | (JP) . |
| 7-159131 | 6/1995 | (JP) . |
| 8-210972 | 8/1996 | (JP) . |
| 2608132 | 2/1997 | (JP) . |
| WO 94/25823 | 11/1994 | (WO) . |
| WO 96/51996 | 5/1996 | (WO) . |

OTHER PUBLICATIONS

H.F. Hazebroek et al., "Automated laser interferometric ellipsometry and precision reflectometry," *J. Phys. E. Sci. Instrum.*, vol. 16, 1983, pp. 654–661.

W. Paik et al., "Exact ellipsometric measurement of thickness and optical properties of a thin light–absorbing film without auxiliary measurements," *Surface Science*, vol. 28, 1971, pp. 61–68.

I. An et al., Simultaneous real time spectroscopic ellipsometry and reflectance for monitoring semiconductor and thin film preparation, Mat. Res. Soc. Symp. Proc., vol. 324, 1994, pp. 33–38.

B.D. Cahan, "Implications of three parameter solutions to the three–layer model," *Surface Science*, vol. 56, 1976, pp. 354–372.

D.K. Burge et al., "Effect of a Thin Surface Film on the Ellipsometric Determination of Optical Constants," *Journal of the Optical Society of America*, vol. 54, Dec. 1964, pp. 1428–1433.

J. Horkans et al., "Electrode potential scanning ellipsometric spectroscopy: study of the formation of the anodic oxide film on noble metals," *Surface Science*, vol. 46, 1974, pp. 1–23.

W.A. McGahan et al., "Combined Spectroscopic Ellipsometry and Reflectometry for Semiconductor Metrology," *Semiconductor Fabtech*, 1996, pp. 183–188.

W.A. McGahan et al., "Combined Spectroscopic Ellipsometry and Reflectometry for Advanced Semiconductor Fabrication Metrology," *SPIE*, vol. 2877, Oct. 1996 SPIE Meeting, 10 pages in length.

E. Elizalde et al., "Determination of the 'Optical' Thickness and of the Filling Factor of Discontinuous Au Films from Photometric and Ellipsometric Measurements," *Optics Communications*, vol. 60, No. 6, Dec. 15, 1986, pp. 378–382.

E. Elizalde et al., "Determination of thickness and optical constants of thin films from photometric and ellipsometric measurements," *Applied Optics*, vol. 25, No. 24, Dec. 15, 1986, pp. 4557–4561.

A. Canillas et al., "An IR phase–modulated ellipsometer using a Fourier transform spectrometer for in situ applications," *Thin Solid Films*, vol. No. 234, 1993, pp. 318–332.

A. Canillas et al., "Phase–modulated ellipsometer using a Fourier transform infrared spectrometer for real time applications," *Rev. Sci. Instrum.*, vol. 64, No. 8, Aug. 1993, pp. 2153–2159.

A. Hamett et al., "An ellipsometric study of polypyrrole films on platinum," *J. Electroanal. Chem.*, vol. 270, 1989, pp. 479–488.

Y. Yen et al., "Method of Determining Optical Constants of Thin Films Using an Infrared Ellipsometer," Optical Interference Coatings Topical Meeting by Optical Society of America, *1998 Technical Digest Series, vol. 6*, Apr. 12–15, 1988, pp. 207–209.

D.E. Aspnes et al., "Multiple determination of the optical constants of thin–film coating materials: a Rh sequel," *Applied Optics*, vol. 25, No. 8, Apr. 15, 1986, pp. 1299–1310.

A. Belkind et al., "Optical properties of $RuO_2$ films deposited by reactive sputtering," *Thin Solid Films*, vol. 207, 1992, pp. 242–247.

A. Gombert et al., "Broadband spectroscopic ellipsometry based on a Fourier transform spectrometer," *Thin Solid Films*, vol. 234, 1993, pp. 352–355.

J.M. Leng et al., "Spectrophotometry and Beam Profile Reflectometry Measurement of Six Layers in an SOI Film Stack," *SPIE*, vol. 2877, 1996, pp. 166–171.

K.Q. Zhang et al., "Determining optical constants using an infrared ellipsometer," *Applied Optics*, vol. 28, No. 14, Jul. 15, 1989, pp. 2929–2934.

S. Gottesfeld et al., "Combined ellipsometric and reflectometric measurements of surface processes on noble metal electrodes," *Surface Science*, vol. 56, 1976, pp. 373–393.

B. Johs et al., "Characterization of Inhomogeneous and Absorbing Thin Films by Combined Spectroscopic Ellipsometry, Reflection, and Transmission Measurements," Optical Interference Coatings Topical Meeting by Optical Society of America, *1992 Technical Digest Series, vol. 15*, Jun. 1–5, 1992, pp. 433–436.

W.A. McGahan et al., "Optical and magneto–optical characterization of TbFeCo thin films in trilayer structures," *J. Appl. Phys.*, vol. 69, No. 8, Apr. 15, 1991, pp. 4568–4570.

R.M.A. Azzam, "Ellipsometric Methods of Characterization of Optical Thin Films," *SPIE*, vol. 642 Thin Film Technologies II, Apr. 15–17, 1986, pp. 198–201.

I. An et al., "Instrumentation considerations in multichannel ellipsometry for real–time spectroscopy," *Thin Solid Films*, vol. 206, 1991, pp. 300–305.

Azzam et al., "Construction, calibration, and testing of a four–dector photopolarimeter," *Rev. sci. Instrum.*, vol. 59, No. 1, Jan. 1988, pp. 84–88.

Johs, "Regression calibration method for rotating element ellipsometers," *Thin Solid Films*, No. 234, 1993, pp. 395–398.

Kawabata et al., "Calibration method of the specific characteristic of an electronic system of a rotating–analyzere ellipsometer," *Applied Optics*, vol. 36, No. 10, Apr. 1, 1997, pp. 2178–2182.

Kino et al., "Mirau correlation microscope," *Applied Optics*, vol. 29, No. 26, Sep. 10, 1990, pp. 3775–3783.

Kouko et al., "Calibration of Two Different Types of Modulators for Application in Spectroscopic Phase Modulated Ellipsometry," *J. Phys. III France*, vol. 5, Aug. 1995, pp. 1211–1227.

Leng et al., "Simultaneous measurement of six layers in a silicon on insulator film stack using spectrophotometry and beam profile reflectometry," *J. Appl. Phys.*, vol. 81, No. 8, Apr. 15, 1997, pp. 3570–3578.

Russev, "Correction for nonlinearity and polarization–dependent sensitivity in the detection system of rotating analyzer ellipsometers," *Applied Optics*, vol. 28, No. 8, Apr. 15, 1989, pp. 1504–1507.

Toney et al., "Calibrating ESCA and Ellipsometry Measurements of Perfluropolyether Lubricant Thickness," *IEEE Transactions on Magnetics*, vol. 34, No. 4, Jul. 1998, pp. 1774–1776.

Xiong et al., "Photoellipsometry: a modulation spectroscopy method applied to n–type GaAs," *Thin Solid Films*, vol. 234, 1993, pp. 399–401.

Azzam et al., text book entitled: "Ellipsometry and Polarized Light," Chapter 3, 1987, pp. 153–268.

H.G. Tompkins, text book entitled: "User's Guide to Ellipsometry," Chapters 1, 2, & 3, 1993, pp. 1–50.

M.J. Rand, "Spectrophotometric Thickness Measurement for Very Thin $SiO_2$ Films on Si," *Journal of Applied Physics*, vol. 41, No. 2, Feb. 1979, pp. 787–789.

A. Ambirajan et al., "Optimum Angles for a Polarimeter: Part I", Optical Engineering, vol. 34 No. 6, pp. 1651–1655, Jun. 1995.

A. Ambirajan et al., Optimum Angles for a Polarimeter: Part II, Optical Engineering, vol. 34 No. 6, pp. 1656–1658, Jun. 1995.

D.E. Aspnes et al. "High Precision Scanning Ellipsometer", Applied Optics, vol. 14, pp. 220–228, Jan. 1975.

I. An et al., "Simultaneous Real Time Spectroscopic Ellipsometry and Reflectance for Monitoring Semiconductor and Thin Film Preparation", Materials Research Society Symposium Proc., vol. 34, pp. 33–38, 1994.

I. Appenzeller, "A New Polarimeter for Faint Astronomical Objects", Yerkes Observatory, Univ. of Chicago, pp. 136–139, Jan. 1967.

D.E. Aspnes, "Alignment of an Optically Active Biplate Compensator", Applied Optics, vol. 10, pp. 2545–2546, Nov. 1971.

D.E. Aspnes et al. "Photomultiplier Linearization and System Stabilization for Photometric Ellipsometers and Polarimeters", SPIE, vol. 112–Optical Polarimetry, pp. 62–66, 1977.

D.E. Aspnes et al., "Rotating–Compensator/Analyzer Fixed–Analyzer Ellipsometer: Analysis and Comparison to Other Automatic Ellipsometers", J. Opt. Soc. Am., vol. 66, No. 9, Sep. 1976, pp. 949–954.

D.K. Burge et al., "Effect of a Thin Surface Film on the Ellipsometric Determination of Optical Constants", Journal of the Optical Society of America, vol. 54, No. 12, pp. 1428–1433, Dec. 1964.

B.D. Cahan "Implications of Three Parameter Solutions to the Three–Layer Model", Surface Science, vol. 56, pp. 354–372, 1976.

D. Clarke et al., "Polarized Light and Optical Measurement", Chapter 4 and bibliography, Pergamon Press Ltd., Oxford, pp. 118–154 and 179–182, 1971.

D. Clarke et al., "A Three–Channel Astronomical Photoelectric Spectropolarimeter", Journal of Scientific Instruments (Journal of Physics E), Series 2, vol. 1, pp. 409–412, 1968.

W. Duncan et al., "Insitu Spectral Ellipsometry for Real–Time Measurement and Control", Applied Surface Science, vol. 63, pp. 9–16, 1993.

Den Boerm J.H.W.G. et al., "Spectroscopic Rotating Compensator Ellipsonetry in the Infrared: Retarder Design and Measurement", Meas. Sci. Technol., vol. 8, Jan. 20, 1997, pp. 484–492.

T. Geherls (ed.), "Planets, Stars and Nebulae Studied with Photopolarimetry", University of Arizona Press, pp. 135–175, 1974.

A. Hamnett et al., "An Ellipsometric Study of Polypyrrole Films on Platinum", J. Electroanal Chem., vol. 270, pp. 479–488, 1989.

P.S. Hauge, "Generalized Rotating–Compensator Ellipsometry", Surface Science, vol. 56, pp. 148–160, 1976.

P.S. Hauge, "Recent Developments in Instrumentation in Ellipsometry", Surface Science, vol. 96, pp. 108–140, 1980.

P.S. Hauge et al., "A Rotating–Compensator Fourier Ellipsometer", Engineering Technology, 5 pages, Mar., 1975.

E. B. Hodgdon, "Theory, Design and Calibration of a UV Spectrophotopolarimeter", Applied Optics, vol. 4, No. 11, pp. 1479–1483, Nov. 1965.

Y.T. Kim et al., "Fast Scanning Spectroelectrochemical Ellipsometry: In–Situ Characterization of Gold Oxide", Surface Science, vol. 233, pp. 341–350, 1990.

H.V. Nguyen et al., "Evolution of the Optical Functions of Thin–Film Aluminum: A Real–Time Spectroscopic Ellipsometry Study", American Physical Society, Physical Review B, vol. 47, No. 7, pp. 3947–3965, Feb. 1993.

W. Paik et al., "Exact Ellipsometric Measurement of Thickness and Optical Properties of a Thin Light–Absorbing Film Without Auxiliary Measurements", Surface Science, vol. 28, pp. 61–68, 1971.

Z. Sekera, "Recent Developments in the Study of the Polarization of Sky Light", Advances in Geophysics, vol. 3, pp. 43–104, 1956.

Aspnes, D.E., "Spectroscopic Ellipsometry of Solids", Optical Properties of Solids: New Developments, ed. by B.C. Seraphin, North–Holland, Amsterdam, 1976, pp. 800–846.

Fanton, J.T. et al., "Multiparameter Measurements of Thin Films Using Beam–Profile Reflectometry", Journal of Applied Physics, vol. 73, Jun. 1, 1993, No. 11, pp. 7035–7040.

Azzam, R.M.A. & Bashara, N.M., "Ellipsometry and Polarized Light", North–Holland, Amsterdam, 1977, pp. 166–255 & 364–411.

R. Carnel, D.L. Pastorius & G.D. Watts, "Ellipsometer Measurement of Thin Film," *IBM Technical Disclosure Bulletin,* vol. 13, No. 9, Feb. 1971, p. 2782.

B. Bhargava & V.V. Shah, "A New Procedure for Alignment & Calibration of an Ellipsometer," *Indian Journal of Pure & Applied Physics,* vol. 14, No. 4, pp. 323–325.

* cited by examiner

THIN FILM OPTICAL MEASUREMENT SYSTEM AND METHOD WITH CALIBRATING ELLIPSOMETER

This application is a continuation of application Ser. No. 09/098,880, filed Jun. 17, 1998 (U.S. Pat. No. 5,900,939), which in turn is a continuation of application Ser. No. 08/890,697, filed Jul. 11, 1997 (U.S. Pat. No. 5,798,837).

FIELD OF THE INVENTION

The present invention relates to optical analyzers, and more particularly to a thin film optical measurement system having a calibrating ellipsometer.

BACKGROUND OF THE INVENTION

There is considerable interest in developing systems for accurately measuring the thickness and/or composition of thin films. The need is particularly acute in the semiconductor manufacturing industry where the thickness of these thin film oxide layers on semiconductor substrates is measured. To be useful, the measurement system must be able to determine the thickness and/or composition of films with a high degree of accuracy. The preferred measurement systems rely on non-contact, optical measurement techniques, which can be performed during the semiconductor manufacturing process without damaging the wafer sample. Such optical measurement techniques include directing a probe beam to the sample, and measuring one or more optical parameters of the reflected probe beam.

In order to increase measurement accuracy and to gain additional information about the target sample, multiple optical measuring devices are incorporated into a single composite optical measurement system. For example, the present assignee has marketed a product called OPTI-PROBE, which incorporates several optical measurement devices, including a Beam Profile Reflectometer (BPR), a Beam Profile Ellipsometer (BPE), and a Broadband Reflective Spectrometer (BRS). Each of these devices measures parameters of optical beams reflected by, or transmitted through, the target sample. The BPR and BPE devices utilize technology described in U.S. Pat. Nos. 4,999,014 and 5,181,080 respectively, which are incorporated herein by reference.

The composite measurement system mentioned above combines the measured results of each of the measurement devices to precisely derive the thickness and composition of the thin film and substrate of the target sample. However, the accuracy of the measured results depends upon precise initial and periodic calibration of the measurement devices in the optical measurement system. Further, recently developed measurement devices have increased sensitivity to more accurately measure thinner films and provide additional information about film and substrate composition. These newer systems require very accurate initial calibration. Further, heat, contamination, optical damage, alignment, etc., that can occur over time in optical measurement devices, affect the accuracy of the measured results. Therefore, periodic calibration is necessary to maintain the accuracy of the composite optical measurement system.

It is known to calibrate optical measurement devices by providing a reference sample having a known substrate, with a thin film thereon having a known composition and thickness. The reference sample is placed in the measurement system, and each optical measurement device measures the optical parameters of the reference sample, and is calibrated using the results from the reference sample and comparing them to the known film thickness and composition. A common reference sample is a "native oxide" reference sample, which is a silicon substrate with an oxide layer formed thereon having a known thickness (about 20 angstroms). After fabrication, the reference sample is kept in a non-oxygen environment to minimize any further oxidation and contamination that changes the thickness of the reference sample film away from the known thickness, and thus reduces the effectiveness of the reference sample for accurate calibration. The same reference sample can be reused to periodically calibrate the measurement system. However, if and when the amount of oxidation or contamination of the reference sample changes the film thickness significantly from the known thickness, the reference sample must be discarded.

For many optical measurement devices, reference samples with known thicknesses have been effective for system calibration. Oxidation and contamination that routinely occurs over time with reference samples is tolerable because the film thickness change resulting from the oxidation/contamination is relatively insignificant compared to the overall thickness of the film (around 100 angstroms). However, new ultra-sensitive optical measurement systems have been recently developed that can measure film layers with thicknesses less than 10 angstroms. These systems require reference samples having film thicknesses on the order of 20 angstroms for accurate calibration. For such thin film reference samples, however, the changes in film layer thickness resulting from even minimal oxidation or contamination are significant compared to the overall "known" film layer thickness, and result in significant calibration error. Therefore, it is extremely difficult, if not impossible, to provide a native oxide reference sample with a known thickness that is stable enough over time to be used for periodic calibration of ultra-sensitive optical measurement systems.

There is a need for a calibration method for ultra-sensitive optical measurement devices that can utilize a reference sample that does not have a stable or known film thickness.

SUMMARY OF THE INVENTION

The present invention is a thin film optical measurement system with a wavelength stable calibration ellipsometer that precisely determines the thickness of a film on a reference sample. The measured results from the calibration ellipsometer are used to calibrate other optical measurement devices in tie thin film optical measurement system. By not having to supply a reference sample with a predetermined known film thickness, a reference sample having a film with a known composition can be repeatedly used to calibrate ultra-sensitive optical measurement devices, even if oxidation or contamination of the reference sample changes the thickness of the film over time.

The calibration reference ellipsometer uses a reference sample that has at least a partially known composition to calibrate at least one other non-contact optical measurement device. The reference ellipsometer includes a light generator that generates a quasi-monochromatic beam of light having a known wavelength and a known polarization for interacting with the reference sample. The beam is directed at a non-normal angle of incidence relative to the reference sample to interact with the reference sample. An analyzer creates interference between S and P polarized components in the light beam after the light beam has interacted with reference sample. A detector measures the intensity of the light after the beam has passed through the analyzer. A processor determines the polarization state of the light beam entering the analyzer from the intensity measured by the detector. The processor then determines optical properties of the reference sample based upon the determined polarization state, the known wavelength of light from the light generator and the at least partially known composition of the reference sample. Wherein the processor operates at least one other non-contact optical measurement device that measures an optical parameter of the reference sample. The processor calibrates the other optical measurement device by comparing the measured optical parameter from the other optical measurement device to the determined optical property from the reference ellipsometer.

Other aspects and features of the present invention will become apparent by a review of the specification, claims and appended figures.

DETAILED DESCRIPTION OF THE PREFERRED EMBODIMENTS

Figure 1:
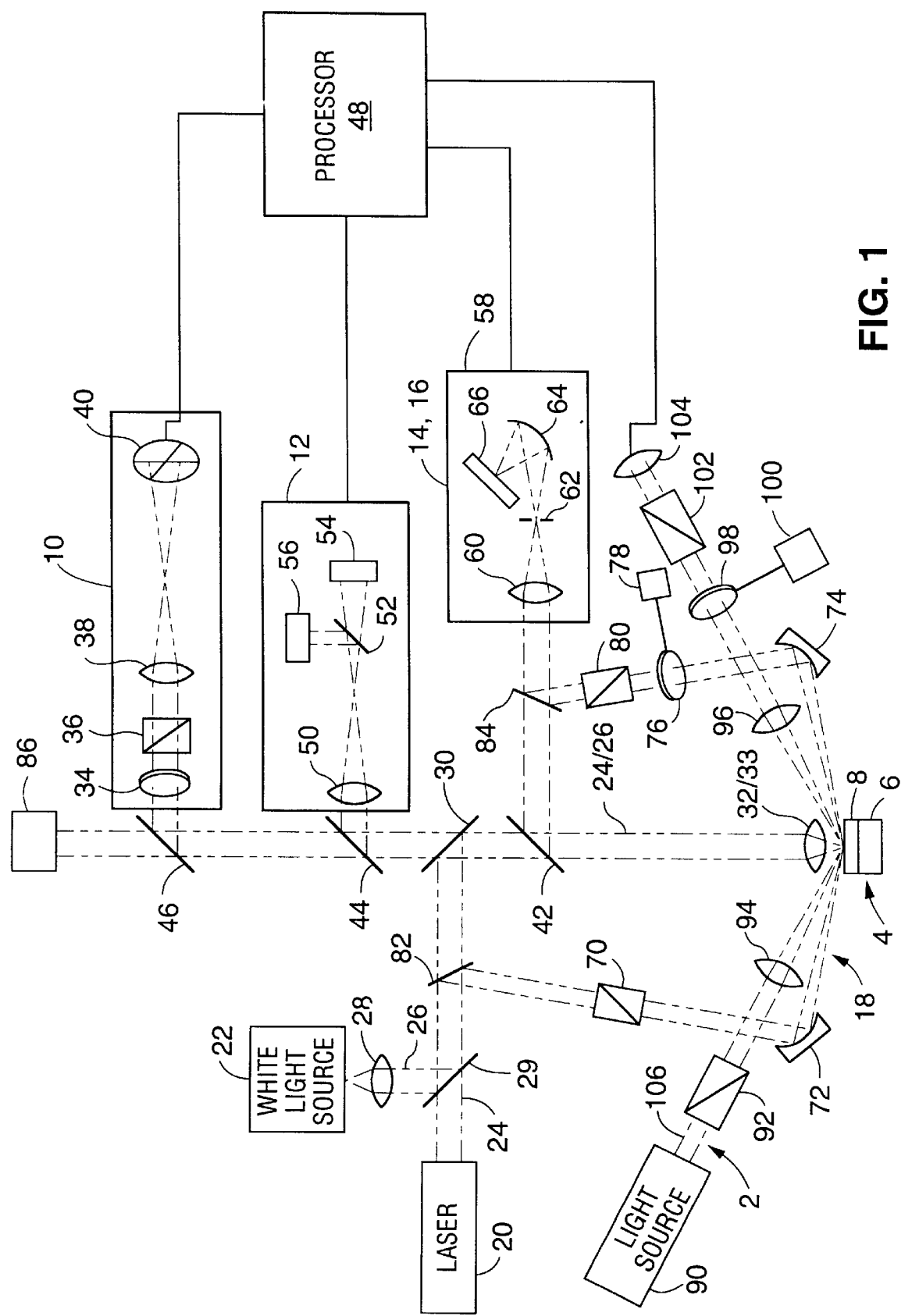
FIG. 1 is a plan view of a composite optical measurement system with the calibration ellipsometer of the present invention.

The present invention is a composite thin film optical measurement system 1 having a wavelength stable reference ellipsometer 2 that is used, in conjunction with a reference sample 4 having a substrate 6 and thin film 8 with known compositions, to calibrate non-contact optical measurement devices contained in the composite thin film optical measurement system 1.

FIG. 1 illustrates the composite optical measurement system 1 that has been developed by the present assignees, which includes five different non-contact optical measurement devices and the reference ellipsometer 2 of the present invention.

Composite optical measurement system 1 includes a Beam Profile Ellipsometer (BPE) 10, a Beam Profile Reflectometer (BPR) 12, a Broadband Reflective Spectrometer (BRS) 14, a Deep Ultra Violet Reflective Spectrometer (DUV) 16, and a Broadband Spectroscopic Ellipsometer (BSE) 18. These five optical measurement devices utilize as few as two optical sources: laser 20 and white light source 22. Laser 20 generates a probe beam 24, and white light source 22 generates probe beam 26 (which is collimated by lens 28 and directed along the same path as probe beam 24 by mirror 29). Laser 20 ideally is a solid state laser diode from Toshiba Corp. which emits a linearly polarized 3 mW beam at 673 nm. White light source 22 is ideally a deuterium-tungsten lamp that produces a 200 mW polychromatic beam that covers a spectrum of 200 nm to 800 nm. The probe beams 24/26 are reflected by mirror 30, and pass through mirror 42 to sample 4.

Figure 2:
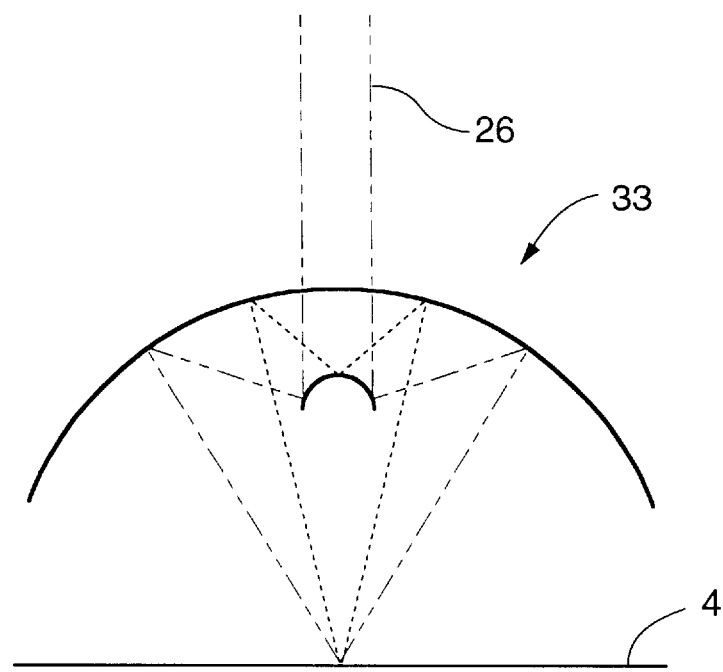
FIG. 2 is a side cross-sectional view of the reflective lens used with the present invention.

The probe beams 24/26, are focused onto the surface of the sample with a lens 32 or lens 33. In the preferred embodiment, two lenses 32/33 are mounted in a turret (not shown) and are alternatively movable into the path of probe beams 24/26. Lens 32 is a spherical, microscope objective lens with a high numerical aperture (on the order of 0.90 NA) to create a large spread of angles of incidence with respect to the sample surface, and to create a spot size of about one micron in diameter. Lens 33 is illustrated in FIG. 2, and is a reflective lens having a lower numerical aperture (on the order of 0.4 NA) and capable of focusing deep UV light to a spot size of about 10–15 microns.

Beam profile ellipsometry (BPE) is discussed in U.S. Pat. No. 5,181,080, issued Jan. 19, 1993, which is commonly owned by the present assignee and is incorporated herein by reference. BPE 10 includes a quarter wave plate 34, polarizer 36, lens 38 and a quad detector 40. In operation, linearly polarized probe beam 24 is focused onto sample 4 by lens 32. Light reflected from the sample surface passes up through lens 32, through mirrors 42, 30 and 44, and directed into BPE 10 by mirror 46. The position of the rays within the reflected probe beam correspond to specific angles of incidence with respect to the sample's surface. Quarter-wave plate 34 retards the phase of one of the polarization states of the beam by 90 degrees. Linear polarizer 36 causes the two polarization states of the beam to interfere with each other. For maximum signal, the axis of the polarizer 36 should be oriented at an angle of 45 degrees with respect to the fast and slow axis of the quarter-wave plate 34. Detector 40 is a quad-cell detector with four radially disposed quadrants that each intercept one quarter of the probe beam and generate a separate output signal proportional to the power of the portion of the probe beam striking that quadrant. This signal represents an integration of the intensities of all the rays having different angles of the incidence with respect to the sample surface. The output signals from each quadrant are sent to a processor 48. As discussed in the U.S. Pat. No. 5,181,080, by monitoring the change in the polarization state of the beam, ellipsometric information, such as $\psi$ and $\Delta$, can be determined. To determine this information, the processor 48 takes the difference between the sums of the output signals of diametrically opposed quadrants, a value which varies linearly with film thickness for very thin films.

Beam profile reflectometry (BPR) is discussed in U.S. Pat. No. 4,999,014, issued on Mar. 12, 1991, which is commonly owned by the present assignee and is incorporated herein by reference. BPR 12 includes a lens 50, beam splitter 52 and two linear detector arrays 54 and 56 to measure the reflectance of the sample. In operation, linearly polarized probe beam 24 is focused onto sample 4 by lens 32, with various rays within the beam striking the sample surface at a range of angles of incidence. Light reflected from the sample surface passes up through lens 32, through mirrors 42 and 30, and directed into BPR 12 by mirror 44. The position of the rays within the reflected probe beam correspond to specific angles of incidence with respect to the sample's surface. Lens 50 spatially spreads the beam two-dimensionally. Beam splitter 52 separates the S and P components of the beam, and detector arrays 54 and 56 are oriented orthogonal to each other to isolate information about S and P polarized light. The higher angles of incidence rays will fall closer to the opposed ends of the arrays. The output from each element in the diode arrays will correspond to different angles of incidence. Detector arrays 54/56 measure the intensity across the reflected probe beam as a function of the angle of incidence with respect to the sample surface. The processor 48 receives the output of the detector arrays 54/56, and derives the thickness and refractive index of the thin film layer 8 based on these angular dependent intensity measurements by utilizing various types of modeling algorithms. Optimization routines which use iterative processes such as least square fitting routines are typically employed. One example of this type of optimization routine is described in "Multiparameter Measurements of Thin Films Using Beam-Profile Reflectivity," Fanton, et. al., Journal of Applied Physics, Vol. 73, No. 11, p.7035, 1993.

Broadband reflective spectrometer (BRS) 14 simultaneously probes the sample 4 with multiple wavelengths of light. BRS 14 uses lens 32 and includes a broadband spectrometer 58 which can be of any type commonly known and used in the prior art. The spectrometer 58 shown in FIG. 1 includes a lens 60, aperture 62, dispersive element 64 and detector array 66. During operation, probe beam 26 from white light source 22 is focused onto sample 4 by lens 32. Light reflected from the surface of the sample passes up through lens 32, and is directed by mirror 42 (through mirror 84) to spectrometer 58. The lens 60 focuses the probe beam through aperture 62, #which defines a spot in the field of view on the sample surface to analyze. Dispersive element 64, such as a diffraction grating, prism or holographic plate, angularly disperses the beam as a function of wavelength to individual detector elements contained in the detector array 66. The different detector elements measure the optical intensities of the different wavelengths of light contained in the probe beam, preferably simultaneously. Alternately, detector 66 can be a CCD camera, or a photomultiplier with suitably dispersive or otherwise wavelength selective optics. It should be noted that a monochrometer could be used to measure the different wavelengths serially (one wavelength at a time) using a single detector element. Further, dispersive element 64 can also be configured to disperse the light as a function of wavelength in one direction, and as a function of the angle of incidence with respect to the sample surface in an orthogonal direction, so that simultaneous measurements as a function of both wavelength and angle of incidence are possible. Processor 48 processes the intensity information measured by the detector array 66.

Deep ultra violet reflective spectrometry (DUV) simultaneously probes the sample with multiple wavelengths of ultra-violet light. DUV 16 uses the same spectrometer 58 to analyze probe beam 26 as BRS 14, except that DUV 16 uses the reflective lens 33 instead of focusing lens 32. To operate DUV 16, the turret containing lenses 32/33 is rotated so that reflective lens 33 is aligned in probe beam 26. The reflective lens 33 is necessary because solid objective lenses cannot sufficiently focus the UV light onto the sample.

Broadband spectroscopic ellipsometry (BSE) is discussed in pending U.S. patent application No. 08/685,606, filed on Jul. 24, 1996, which is commonly owned by the present assignee and is incorporated herein by reference. BSE (18) includes a polarizer 70, focusing mirror 72, collimating mirror 74, rotating compensator 76, and analyzer 80. In operation, mirror 82 directs at least part of probe beam 26 to polarizer 70, which creates a known polarization state for the probe beam, preferably a linear polarization. Mirror 72 focuses the beam onto the sample surface at an oblique angle, ideally on the order of 70 degrees to the normal of the sample surface. Based upon well known ellipsometric principles, the reflected beam will generally have a mixed linear and circular polarization state after interacting with the sample, based upon the composition and thickness of the sample's film 8 and substrate 6. The reflected beam is collimated by mirror 74, which directs the beam to the rotating compensator 76. Compensator 76 introduces a relative phase delay δ (phase retardation) between a pair of mutually orthogonal polarized optical beam components. Compensator 8 is rotated at an angular velocity ω about an axis substantially parallel to the propagation direction of the beam, preferably by an electric motor 78. Analyzer 80, preferably another linear polarizer, mixes the polarization states incident on it. By measuring the light transmitted by analyzer 80, the polarization state of the reflected probe beam can be determined. Mirror 84 directs the beam to spectrometer 58, which simultaneously measures the intensities of the different wavelengths of light in the reflected probe beam that pass through the compensator/analyzer combination. Processor 48 receives the output of the detector 66, and processes the intensity information measured by the detector 66 as a function of wavelength and as a function of the azimuth (rotational) angle of the compensator 76 about its axis of rotation, to solve the ellipsometric values ψ and Δ as described in U.S. patent application No. 08/685,606.

Detector/camera 86 is positioned above mirror 46, and can be used to view reflected beams off of the sample 4 for alignment and focus purposes.

In order to calibrate BPE 10, BPR 12, BRS 14, DUV 16, and BSE 18, the composite optical measurement system 1 includes the wavelength stable calibration reference ellipsometer 2 used in conjunction with a reference sample 4. Ellipsometer 2 includes a light source 90, polarizer 92, lenses 94 and 96, rotating compensator 98, analyzer 102 and detector 104.

Figure 3:
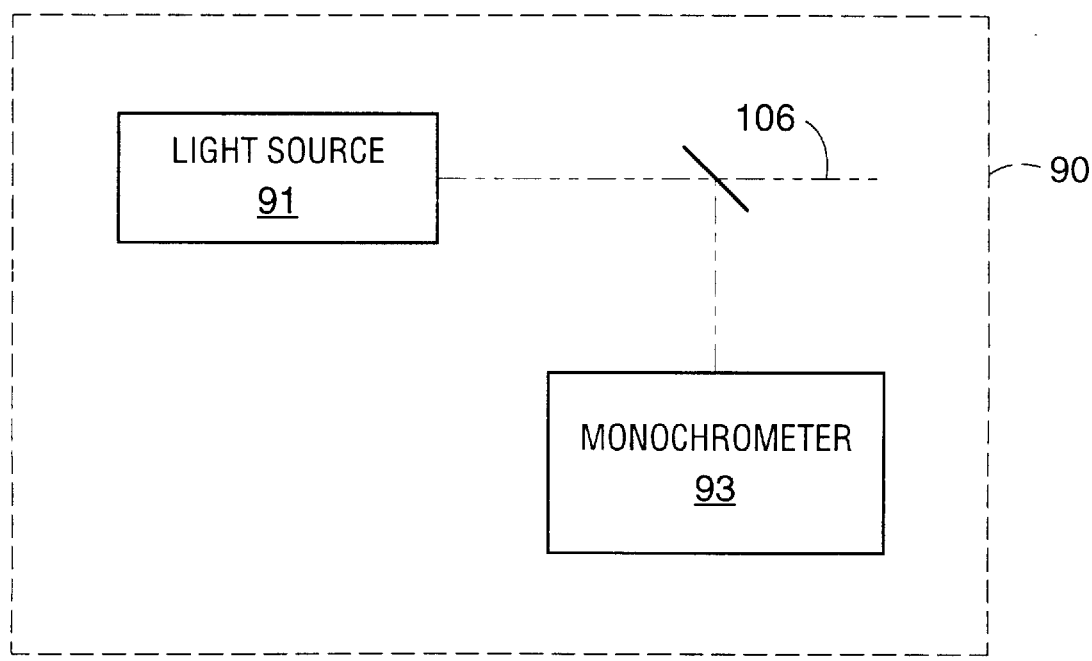
FIG. 3 is a plan view of an alternate embodiment of the light source for the calibration ellipsometer of the present invention.

Light source 90 produces a quasi-monochromatic probe beam 106 having a known stable wavelength and stable intensity. This can be done passively, where light source 90 generates a very stable output wavelength which does not vary over time (i.e. varies less than 1%). Examples of passively stable light sources are a helium-neon laser, or other gas discharge laser systems. Alternately, a non-passive system can be used as illustrated in FIG. 3 where the light source 90 includes a light generator 91 that produces light having a wavelength that is not precisely known or stable over time, and a monochrometer 93 that precisely measures the wavelength of light produced by light generator 91. Examples of such light generators include laser diodes, or polychromatic light sources used in conjunction with a color filter such as a grating. In either case, the wavelength of beam 106, which is a known constant or measured by monochrometer 93, is provided to processor 48 so that ellipsometer 2 can accurately calibrate the optical measurement devices in system 1.

The beam 106 interacts with polarizer 92 to create a known polarization state. In the preferred embodiment, polarizer 92 is a linear polarizer made from a quartz Rochon prism, but in general the polarization does not necessarily have to be linear, nor even complete. Polarizer 92 can also be made from calcite. The azimuth angle of polarizer 92 is oriented so that the plane of the electric vector associated with the linearly polarized beam exiting from the polarizer 92 is at a known angle with respect to the plane of incidence (defined by the propagation direction of the beam 106 and the normal to the surface of sample 4). The azimuth angle is preferably selected to be on the order of 30 degrees because the sensitivity is optimized when the reflected intensities of the P and S polarized components are approximately balanced. It should be noted that polarizer 92 can be omitted if the light source 90 emits light with the desired known polarization state.

The beam 106 is focused onto the sample 4 by lens 94 at an oblique angle. For calibration purposes, reference sample 4 ideally consists of a thin oxide layer 8 having a thickness d, formed on a silicon substrate 6. However, in general, the sample 4 can be any appropriate substrate of known composition, including a bare silicon wafer, and silicon wafer substrates having one or more thin films thereon. The thickness d of the layer 8 need not be known, or be consistent between periodic calibrations. The useful light from probe beam 106 is the light reflected by the sample 4 symmetrically to the incident beam about the normal to the sample surface. It is noted however that the polarization state of nonspecularly scattered radiation can be determined by the method of the present invention as well. The beam 106 is ideally incident on sample 4 at an angle on the order of 70 degrees to the normal of the sample surface because sensitivity to sample properties is maximized in the vicinity of the Brewster or pseudo-Brewster angle of a material. Based upon well known ellipsometric principles, the reflected beam will generally have a mixed linear and circular polarization state after interacting with the sample, as compared to the linear polarization state of the incoming beam. Lens 96 collimates beam 106 after its reflection off of the sample 4.

The beam 106 then passes through the rotating compensator (retarder) 98, which introduces a relative phase delay $\delta$ (phase retardation) between a pair of mutually orthogonal polarized optical beam components. The amount of phase retardation is a function of the wavelength, the dispersion characteristics of the material used to form the compensator, and the thickness of the compensator. Compensator 98 is rotated at an angular velocity $\omega$ about an axis substantially parallel to the propagation direction of beam 106, preferably by an electric motor 100. Compensator 98 can be any conventional wave-plate compensator, for example those made of crystal quartz. The thickness and material of the compensator 98 are selected such that a desired phase retardation of the beam is induced. In the preferred embodiment, compensator 98 is a bi-plate compensator constructed of two parallel plates of anisotropic (usually birefringent) material, such as quartz crystals of opposite handedness, where the fast axes of the two plates are perpendicular to each other and the thicknesses are nearly equal, differing only by enough to realize a net first-order retardation for the wavelength produced by the light source 90.

Beam 106 then interacts with analyzer 102, which serves to mix the polarization states incident on it. In this embodiment, analyzer 102 is another linear polarizer, preferably oriented at an azimuth angle of 45 degrees relative to the plane of incidence. However, any optical device that serves to appropriately mix the incoming polarization states can be used as an analyzer. The analyzer 102 is preferably a quartz Rochon or Wollaston prism. The rotating compensator 98 changes the polarization state of the beam as it rotates such that the light transmitted by analyzer 102 is characterized by:

$$
\begin{aligned}
I(t) = & \; (1/2)[\,|E_x|^2\,(1 + \cos^2(\delta/2) + |E_y|^2\sin^2(\delta/2)] \\
& - Im(E_x E_y *)\sin\delta\sin(2\omega t) \\
& + Re(E_x E_y *)\sin^2(\delta/2)\sin(4\omega t) \\
& + (1/2)(\,|E_x|^2 - |E_y|^2)\sin^2(\delta/2))\cos(4\omega t) \\
= & \; a_o + b_2\sin(2\omega t) + a_4\cos(4\omega t) + b_4\sin(4\omega t),
\end{aligned}
\tag{1}
$$

$$\tag{2}$$

where $E_x$ and $E_y$ are the projections of the incident electric field vector parallel and perpendicular, respectively, to the transmission axis of the analyzer, $\delta$ is the phase retardation of the compensator, and $\omega$ is the angular rotational frequency of the compensator.

For linearly polarized light reflected at non-normal incidence from the specular sample, we have $$E_x = r_p \cos P \tag{3a}$$

$$E_y = r_s \sin P \tag{3b}$$

where P is the azimuth angle of the incident light with respect to the plane of incidence. The coefficients $a_0$, $b_2$, $a_4$, and $b_4$ can be combined in various ways to determine the complex reflectance ratio:

$$r_p/r_s = \tan\psi e^{i\Delta}. \tag{4}$$

It should be noted that the compensator 98 can be located either between the sample 4 and the analyzer 102 (as shown in FIG. 1), or between the sample 4 and the polarizer 92, with appropriate and well known minor changes to the equations. It should also be noted that polarizer 70, lenses 94/96, compensator 98 and polarizer 102 are all optimized in their construction for the specific wavelength of light produced by light source 90, which maximizes the accuracy of ellipsometer 2.

Beam 106 then enters detector 104, which measures the intensity of the beam passing through the compensator/analyzer combination. The processor 48 processes the intensity information measured by the detector 104 to determine the polarization state of the light after interacting with the analyzer, and therefore the ellipsometric parameters of the sample. This information processing includes measuring beam intensity as a function of the azimuth (rotational) angle of the compensator about its axis of rotation. This measurement of intensity as a function of compensator rotational angle is effectively a measurement of the intensity of beam 106 as a function of time, since the compensator angular velocity is usually known and a constant.

By knowing the composition of reference sample 4, and by knowing the exact wavelength of light generated by light source 90, the optical properties of reference sample 4, such as film thickness d, refractive index and extinction coefficients, etc., can be determined by ellipsometer 2. If the film is very thin, such as less than or equal to about 20 angstroms, the thickness d can be found to first order in d/$\lambda$ by solving $$\frac{\rho - \rho_o}{\rho_o} = \frac{4\pi i d \cos\theta}{\lambda} \frac{\epsilon_s(\epsilon_s - \epsilon_o)(\epsilon_o - \epsilon_a)}{\epsilon_o(\epsilon_s - \epsilon_a)(\epsilon_s \cot^2\theta - \epsilon_a)}, \tag{5}$$

where $$\rho_o = \tan\Psi_o e^{i\Delta_o} \tag{6}$$

$$= \frac{\sin^2\theta - \cos\theta(\epsilon_s/\epsilon_a - \sin^2\theta)^{1/2}}{\sin^2\theta + \cos\theta(\epsilon_s/\epsilon_a - \sin^2\theta)^{1/2}} \tag{7}$$

which is the value of $\rho = \tan\Psi e^{i\Delta}$ for d=0. Here, $\lambda$=wavelength of light; and $\epsilon_s, \epsilon_o$ and $\epsilon a$, are the dielectric functions of the substrate, thin oxide film, and ambient, respectively, and $\theta$ is the angle of incidence.

If the film thickness d is not small, then it can be obtained by solving the equations $$\rho = r_p/r_s, \text{ where} \tag{8}$$

-continued $$r_p = \frac{r_{p,oa} + Zr_{p,so}}{1 + Zr_{p,oa}r_{p,so}} \quad (9)$$

$$r_s = \frac{r_{s,oa} + Zr_{s,so}}{1 + Zr_{s,oa}r_{s,so}} \quad (10)$$

and where $$Z = e^{2ik\,d}, \quad (11)$$

$$ck_{o\perp}/\omega = n_{o\perp} = (\epsilon_o/\epsilon_a - \sin^2\theta)^{1/2} \quad (12)$$

$$r_{s,so} = \frac{n_{o\perp} - n_{s\perp}}{n_{o\perp} + n_{s\perp}} \quad (13)$$

$$r_{s,oa} = \frac{n_{a\perp} - n_{o\perp}}{n_{a\perp} + n_{o\perp}} \quad (14)$$

$$r_{p,so} = \frac{\epsilon_o n_{o\perp} - \epsilon_o n_{s\perp}}{\epsilon_o n_{o\perp} + \epsilon_o n_{s\perp}} \quad (15)$$

$$r_{p,oa} = \frac{\epsilon_o n_{a\perp} - \epsilon_a n_{o\perp}}{\epsilon_o n_{a\perp} + \epsilon_a n_{o\perp}} \quad (16)$$

and in general $$n_{j\perp} = (\epsilon_j - \epsilon_a \sin^2\theta)^{1/2}, \quad (17)$$

where j is a or a. These equations generally have to be solved numerically for d and $n_o$ simultaneously, using $\epsilon_s$, $\epsilon_a$, $\Lambda$, and $\theta$, which are known.

Once the thickness d of film 8 has been determined by ellipsometer 2, then the same sample 4 is probed by the other optical measurement devices BPE 10, BPR 12, BRS 14, DUV 16, and BSE 18 which measure various optical parameters of the sample 4. Processor 48 then calibrates the processing variables used to analyze the results from these optical measurement devices so that they produce accurate results. For each of these measurement devices, there are system variables that affect the measured data and need to be accounted for before an accurate measurement of other samples can be made. In the case of BPE 10, the most significant variable system parameter is the phase shift that occurs due to the optical elements along the BPE optical path. Environmental changes to these optical elements result in an overall drift in the ellipsometric parameter $\Delta$, which then translates into a sample thickness drift calculated by the processor 48 from BPE 10. Using the measured optical parameters of BPE 10 on reference sample 4, and using Equation 5 and the thickness of film 8 as determined from calibration ellipsometer 2, the processor 48 calibrates BPE 10 by deriving a phase offset which is applied to measured results from BPE 10 for other samples, thereby establishing an accurate BPE measurement. For BSE 18, multiple phase offsets are derived for multiple wavelengths in the measured spectrum.

For the remaining measurement devices, BPR 12, BRS 14 and DUV 16, the measured reflectances can also be affected by environmental changes to the optical elements in the beam paths. Therefore, the reflectances $R_{ref}$ measured by BPR 12, BRS 14 and DUV 16 for the reference sample 4 are used, in combination with the measurements by ellipsometer 2, to calibrate these systems. Equations 9–17 are used to calculate the absolute reflectances $R^c_{ref}$ of reference sample 4 from the measured results of ellipsometer 2. All measurements by the BPR/BRS/DUV devices of reflectance ($R_s$) for any other sample are then scaled by processor 48 using the normalizing factor in equation 18 below to result in accurate reflectances R derived from the BPR, BRS and DUV devices:

$$R = R_s \, (R^c_{ref}/R_{ref}) \quad (18)$$

In the above described calibration techniques, all system variables affecting phase and intensity are determined and compensated for using the phase offset and reflectance normalizing factor discussed above, thus rendering the optical measurements made by these calibrated optical measurement devices absolute.

The above described calibration techniques are based largely upon calibration using the derived thickness d of the thin film. However, calibration using ellipsometer 2 can be based upon any of the optical properties of the reference sample that are measurable or determinable by ellipsometer 2 and/or are otherwise known, whether the sample has a single film thereon, has multiple films thereon, or even has no film thereon (bare sample).

The advantage of the present invention is that a reference sample having no thin film thereon, or having thin film thereon with an unknown thickness which may even vary slowly over time, can be repeatedly used to accurately calibrate ultra-sensitive optical measurement devices. The output of light source 90 can also be used to calibrate the wavelength measurements made by spectrometer 58. The sample 4 can be tipped, or replaced by a tipped mirror, to direct beam 106 up to mirror 42 and to dispersion element 64. By knowing the exact wavelength of light produced by light source 90, processor 48 can calibrate the output of detector 66 by determining which pixel(s) corresponds to that wavelength of light.

It should be noted that the calibrating ellipsometer 2 of the present invention is not limited to the specific rotating compensator ellipsometer configuration discussed above. The scope of the present invention includes any ellipsometer configuration in conjunction with the light source 90 (having a known wavelength) that measures the polarization state of the beam after interaction with the sample and provides the necessary information about sample 4 for calibrating non-contact optical measurement devices.

For example, another ellipsometric configuration is to rotate polarizer 92 or analyzer 100 with motor 100, instead of rotating the compensator 98. The above calculations for solving for thickness d still apply.

In addition, null ellipsometry, which uses the same elements as ellipsometer 2 of FIG. 1, can be used to determine the film thickness d for calibration purposes. The ellipsometric information is derived by aligning the azimuthal angles of these elements until a null or minimum level intensity is measured by the detector 104. In the preferred null ellipsometry embodiment, polarizers 92 and 102 are linear polarizers, and compensator 98 is a quarter-wave plate. Compensator 98 is aligned so that its fast axis is at an azimuthal angle of 45 degrees relative to the plane of incidence of the sample 4. Polarizer 92 has a transmission axis that forms an azimuthal angle P relative to the plane of incidence, and polarizer 102 has a transmission axis that forms an azimuthal angle A relative to the plane of incidence. Polarizers 92 and 102 are rotated about beam 106 such that the light is completely extinguished (minimized) by the analyzer 102. In general, there are two polarizer 92/102 orientations ($P_1$, $A_1$) and ($P_2$, $A_2$) that satisfy this condition and extinguish the light. With the compensator inducing a 90 degree phase shift and oriented with an azimuthal angle at 45 degree relative to the plane of incidence, we have:

$$P_2 = P_1 \pm \pi/2 \quad (19)$$

$$A_2 = -A_1 \quad (20)$$

$$\psi = A_1 \geq 0 \quad (21)$$

(where $A_1$ is the location for which A is positive).

$$\Delta = 2P_1 + \pi/2 \quad (22)$$

which, when combined with equations 5–10, allows the processor to solve for thickness d.

Null ellipsometry is very accurate because the results depend entirely on the measurement of mechanical angles, and are independent of intensity. Null ellipsometry is further discussed by R. M. A. Azzam and N. M. Bashara, in Ellipsometry and Polarized Light (North-Holland, Amsterdam, 1977); and by D. E. Aspnes, in Optical Properties of Solids: New Developments, ed. B. O. Seraphin (North-Holland, Amsterdam, 1976), p. 799.

It is also conceivable to omit compensator 98 from ellipsometer 2, and use motor 100 to rotate polarizer 92 or analyzer 102. Either the polarizer 92 or the analyzer 102 is rotated so that the detector signal can be used to accurately measure the linear polarization component of the reflected beam. Then, the circularly polarized component is inferred by assuming that the beam is totally polarized, and what is not linearly polarized must be circularly polarized. Such an ellipsometer, commonly called a rotating-polarizer or rotating-analyzer ellipsometer, is termed "an incomplete" polarimeter, because it is insensitive to the handedness of the circularly polarized component and exhibits poor performance when the light being analyzed is either nearly completely linearly polarized or possesses a depolarized component. However, using UV light from source 90, the substrate of materials such as silicon contribute enough to the overall phase shift of the light interacting with the sample that accurate results can be obtained without the use of a compensator. In such a case, the same formulas above can be used to derive thickness d, where the phase shift induced by the compensator is set to be zero.

Figure 4:
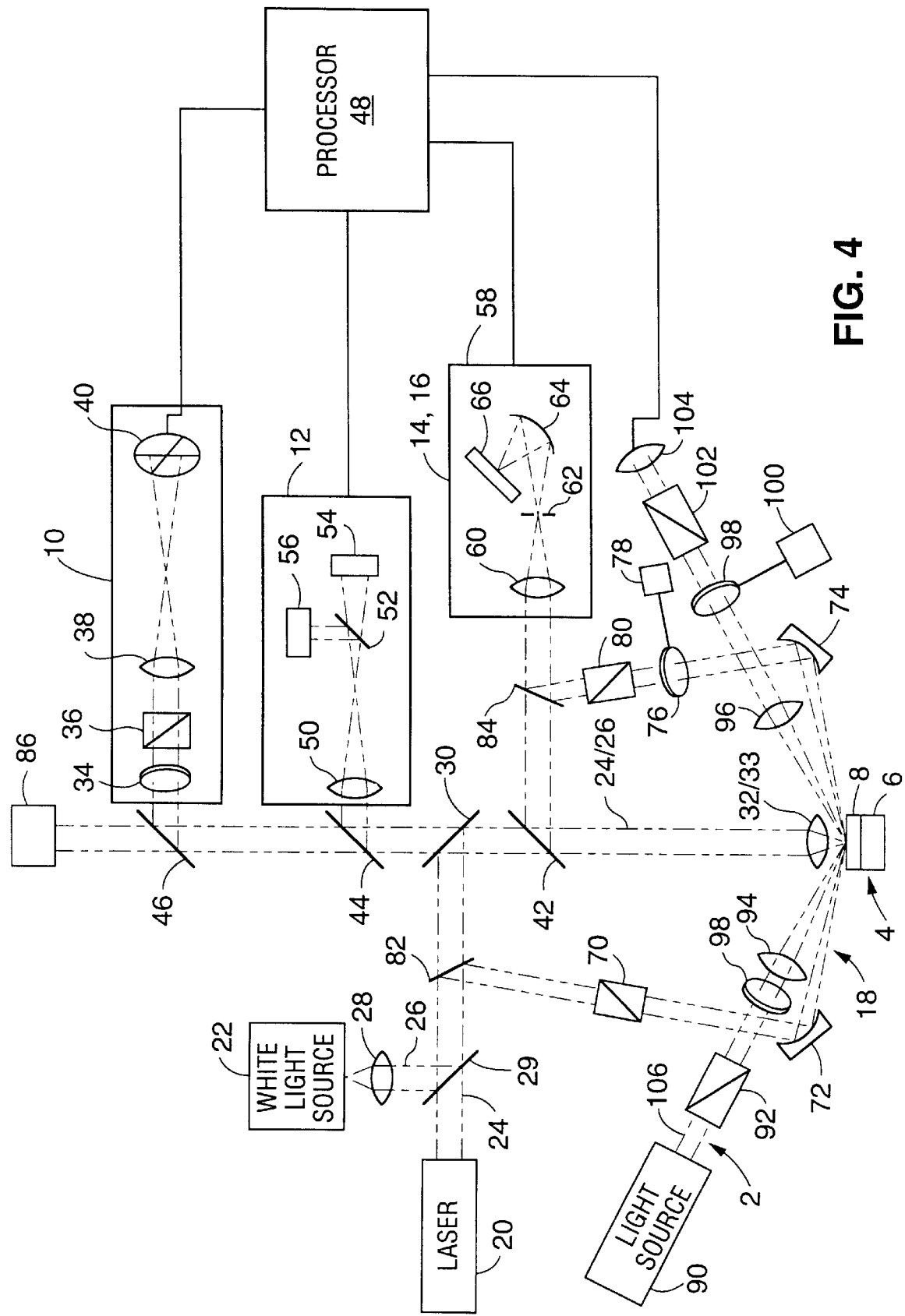
FIG. 4 is a plan view of the composite optical measurement system with multiple compensators in the calibration ellipsometer of the present invention.

It is to be understood that the present invention is not limited to the embodiments described above and illustrated herein, but encompasses any and all variations falling within the scope of the appended claims. For example, beams 24, 26, and/or 106 can be transmitted through the sample, where the beam properties (including the beam polarization state) of the transmitted beam are measured. Further, a second compensator can be added, where the first compensator is located between the sample and the analyzer, and the second compensator located between the sample and the light source 90, as illustrated in FIG. 4. These compensators could be static or rotating. In addition, to provide a static or varying retardation between the polarization states, compensator 98 can be replaced by a non-rotating optoelectronic element or photo-elastic element, such as a piezoelectric cell retarder which are commonly used in the art to induce a sinusoidal or static phase retardation by applying a varying or static voltage to the cell.

What is claimed is:

1. An apparatus for evaluating characteristics of a semiconductor test sample comprising:

a measurement device module including a light source for generating a probe beam directed to reflect off the test sample and wherein the probe beam is focused so that rays within the probe beam strike the sample at a plurality of different angels of incidence and further including a detector for monitoring the changes in the intensity of the reflected probe beam as a function of angle of incidence;

a processor for evaluating the test sample based on the measured changes of the probe beam; and a calibration module including a reference sample and an off-axis ellipsometer having a wavelength stable, narrowband light source for measuring the reference sample and wherein said apparatus is arranged so that the reference sample is also measured by the measurement device module and wherein the processor utilizes the measurements of the reference sample by both the off-axis ellipsometer and the measurement device module to calibrate the measurement device module for subsequent measurements of test samples.

2. An apparatus as recited in claim 1 wherein said detector monitors changes of intensity of the reflected probe beam as a function of position within the probe beam to derive information related to multiple angles of incidence.

3. An apparatus as recited in claim 2 wherein said detector includes a linear array of detector elements for monitoring the intensity of the rays within the reflected probe beam as a function of position.

4. An apparatus as recited in claim 2 wherein the narrowband light source is defined by a gas discharge laser.

5. An apparatus as recited in claim 4 wherein said gas discharge laser is a helium-neon laser.

6. An apparatus as recited in claim 2 wherein said narrowband light source is defined by a laser diode.

7. An apparatus as recited in claim 2 wherein the narrowband wavelength source produces light have a stable known wavelength to within one percent.

8. An apparatus as recited in claim 2 wherein the reference sample is defined by a substrate having an oxide layer thereon wherein the composition of the oxide is known prior to measurement while the thickness of the oxide layer is unknown prior to measurement.

9. A method of operating an optical inspection apparatus to analyze the characteristics of a semiconductor test sample, wherein the inspection apparatus includes a measurement device module having a primary light source for generating a probe beam directed to reflect off the test sample and wherein the probe beam is focused so that rays within the probe beam strike the sample at a plurality of different angles of incidence and further including a detector for monitoring the changes in the intensity of the reflected probe as a function of angle of incidence, said inspection apparatus further including a calibration module incorporating an off-axis ellipsometer having a stable wavelength narrowband light source, said calibration module further including a reference sample, said method comprising the steps of:

measuring the reference sample with the off-axis ellipsometer;

measuring the reference sample with the measurement device module;

analyzing the characteristics of the reference sample using the measurements obtained from both the off-axis ellipsometer and the measurement device module;

comparing the analyses of the characteristics of the reference sample derived from measurements obtained from the off-axis ellipsometer and the measurement device module;

calibrating the measurement device module based on the comparison of the analyses of the characteristics of the reference sample; and measuring and analyzing a test sample with the calibrated measurement device module.

10. A method as recited in claim 9 wherein the detector of the measurement device module monitors changes of intensity of the reflected probe beam as a function of position within the probe beam to derive information related to multiple angles of incidence.

11. A method as recited in claim 10 wherein the detector of the measurement device module includes a linear array of detector elements for monitoring the intensity of the rays within the reflected probe beam as a function of position.

12. A method as recited in claim 10 wherein the reference sample is defined by a substrate having an oxide layer thereon.

13. A method as recited in claim 12 wherein during said step of analyzing the reference sample, the thickness of the oxide layer of the reference sample determined based on the measurements made with the measurement device module is compared with the thickness of the oxide layer determined based on the measurements made with the off-axis ellipsometer in order to calibrate the measurement device module.

14. An apparatus for evaluating characteristics of a semiconductor test sample comprising:
   a measurement device module including a light source for generating a probe beam directed to reflect off the test sample and wherein the probe beam is focused so that rays within the probe beam strike the sample at a plurality of different angles of incidence and further including a detector for monitoring the changes in the polarization state of the reflected probe beam;
   a processor for evaluating the test sample based on the measured changes of the probe beam; and
   a calibration module including a reference sample and an off-axis ellipsometer having a wavelength stable, narrowband light source for measuring the reference sample and wherein said apparatus is arranged so that the reference sample is also measured by the measurement device module and wherein the processor utilizes the measurements of the reference sample by both the off-axis ellipsometer and the measurement device module to calibrate the measurement device module for subsequent measurements of test samples.

15. An apparatus as recited in claim 14 wherein the detector of the measurement device module generates an output which represents an integration of the intensity variations of rays having different angles of incidence.

16. An apparatus as recited in claim 15 wherein said measurement device module further includes a retarder and an analyzer and wherein the detector measures intensity along two orthogonal axes to determine ellipsometric information about the sample.

17. An apparatus as recited in claim 16 wherein the detector of the measurement device module includes a quad-cell and wherein the processor calculates the difference between the sums of diametrically opposed quadrants to determine ellipsometric information about the sample.

18. An apparatus as recited in claim 14 wherein the narrowband light source is defined by a gas discharge laser.

19. An apparatus as recited in claim 18 wherein said gas discharge laser is a helium-neon laser.

20. An apparatus as recited in claim 14 wherein said narrowband light source is defined by a laser diode.

21. An apparatus as recited in claim 14 wherein the narrowband wavelength source produces light have a stable known wavelength to within one percent.

22. An apparatus as recited in claim 14 wherein the reference sample is defined by a substrate having an oxide layer thereon wherein the composition of the oxide is known prior to measurement while the thickness of the oxide layer is unknown prior to measurement.

23. A method of operating an optical inspection apparatus to analyze the characteristics of a semiconductor test sample, wherein the inspection apparatus includes a measurement device module having a primary light source for generating a probe beam directed to reflect off the test sample and wherein the probe beam is focused so that rays within the probe beam strike the sample at a plurality of different angles of incidence and further including a detector for monitoring the changes in the polarization state of the reflected probe, said inspection apparatus further including a calibration module incorporating an off-axis ellipsometer having a stable wavelength narrowband light source, said calibration module further including a reference sample, said method comprising the steps of:
   measuring the reference sample with the off-axis ellipsometer;
   measuring the reference sample with the measurement device module;
   analyzing the characteristics of the reference sample using the measurements obtained from both the off-axis ellipsometer and the measurement device module;
   comparing the analyses of the characteristics of the reference sample derived from measurements obtained from the off-axis ellipsometer and the measurement device module;
   calibrating the measurement device module based on the comparison of the analyses of the characteristics of the reference sample; and
   measuring and analyzing a test sample with the calibrated measurement device module.

24. A method as recited in claim 23 wherein the detector of the measurement device module generates an output which represents an integration of the intensity variations of rays having different angles of incidence.

25. A method as recited in claim 24 wherein said measurement device module further includes a retarder and an analyzer. and wherein the detector measures intensity along two orthogonal axes to determine ellipsometric information about the sample.

26. A method as recited in claim 25 wherein the detector of the measurement device module includes a quad-cell and wherein the processor calculates the difference between the sums of diametrically opposed quadrants to determine ellipsometric information about the sample.

27. A method as recited in claim 24 wherein the reference sample is defined by a substrate having an oxide layer thereon.

28. A method as recited in claim 24 wherein during said step of analyzing the reference sample, the thickness of the oxide layer of the reference sample determined based on the measurements made with the measurement device module is compared with the thickness of the oxide layer determined based on the measurements made with the off-axis ellipsometer in order to calibrate the measurement device module.

* * * * *